United States Patent
Sukkar Picedi-Benettini

(10) Patent No.: US 10,737,047 B2
(45) Date of Patent: Aug. 11, 2020

(54) DEVICE FOR INHIBITING AT LEAST PARTIALLY THE SENSE OF SMELL

(71) Applicant: Samir Sukkar Picedi-Benettini, Genoa (IT)

(72) Inventor: Samir Sukkar Picedi-Benettini, Genoa (IT)

(*) Notice: Subject to any disclaimer, the term of this patent is extended or adjusted under 35 U.S.C. 154(b) by 256 days.

(21) Appl. No.: 16/000,329

(22) Filed: Jun. 5, 2018

(65) Prior Publication Data
US 2019/0366021 A1   Dec. 5, 2019

(51) Int. Cl.
*A61F 5/00*  (2006.01)
*A61M 15/08* (2006.01)
*A61M 21/00* (2006.01)
*A62B 23/06* (2006.01)

(52) U.S. Cl.
CPC ......... *A61M 15/085* (2014.02); *A61F 5/0003* (2013.01); *A61M 2021/0016* (2013.01); *A62B 23/06* (2013.01)

(58) Field of Classification Search
CPC ..... A62B 23/06; A61M 15/08; A61M 15/085; A61M 2210/0618; A61M 2021/0005; A61M 2205/588; A61M 2021/0016; A61F 5/0003; A61H 2205/023; A61K 9/0043; A63J 2005/008
See application file for complete search history.

(56) References Cited

U.S. PATENT DOCUMENTS

| | | |
|---|---|---|
| 2008/0092896 A1 | 4/2008 | Jackson |
| 2009/0250067 A1 | 10/2009 | Arnon |
| 2011/0100369 A1 | 5/2011 | Zhang et al. |
| 2013/0174849 A1* | 7/2013 | Atkinson ............... A62B 23/06 128/206.11 |

* cited by examiner

*Primary Examiner* — Brian A Dukert
*Assistant Examiner* — Rebecca Lynee Zimmerman
(74) *Attorney, Agent, or Firm* — Vorys, Sater, Seymour and Pease LLP

(57) ABSTRACT

A device for inhibiting at least partially the sense of smell including a solid body is provided for having a main extension along a main plane in which it has a main shape including: an upper portion extending mainly in the longitudinal direction and including a first upper edge substantially flat and aligned with the longitudinal direction, a lower portion protruding at least partially in said vertical direction and downwards, a rear portion extending diagonally in relation to the longitudinal and vertical directions and including a second upper edge in direct contact with the first upper edge and extending in a direction inclined at an angle of between 20° and 70° with respect to the longitudinal direction; the first upper edge extends, in addition, in the transverse direction, more than the remaining part of the solid body.

10 Claims, 2 Drawing Sheets

DEVICE FOR INHIBITING AT LEAST PARTIALLY THE SENSE OF SMELL

TECHNICAL BACKGROUND

The present invention relates to a device for inhibiting at least partially the sense of smell, for the treatment of obesity, and the sense of taste in order to cause satiety associated with the absence of the hedonic component of food, to provide a new instrument for the treatment of obesity, of the type comprising a solid body suitable to be placed inside the nostrils, in the vault of the nasal cavity between the upper turbinate and septum so as to superpose the olfactory mucosa causing a temporary anosmia and having a main extension along a main plane in use substantially parallel to the sagittal plane of the human body, the main plane defining a longitudinal direction and a vertical direction lying in the main plane and mutually perpendicular, and a transverse direction perpendicular to the main plane.

DESCRIPTION OF THE PRIOR ART

The problem of obesity is currently known of and affects western countries in particular. The World Health Organisation actually forecasts that obesity may soon replace the more traditional public health problems such as malnutrition and infectious diseases (Loscalzo, Joseph; Fauci, Anthony S.; Braunwald, Eugene; Dennis L. Kasper; Hauser, Stephen L; Longo, Dan L., Harrison's principles of internal medicine, McGraw-Hill Medical, 2008, ISBN 0-07-146633-9).

Obesity is modestly combated, as well as psychologically, by different methods that also go beyond the simple imposition of a diet or physical activity.

In particular, the reduction in the volume of the stomach by applying an elastic, inserting a balloon or otherwise is known of.

The reduction in the volume of the stomach make the patient feel satiated sooner. Other methods yet are also known of.

One of the recently developed obesity remedies is the inhibition of the sense of smell.

Smell, in fact, is the basis of taste and contributes very much to the perception of taste itself. As is known in fact, a mere cold is enough to greatly reduce the sense of taste.

The sense of taste is in turn largely responsible for the uncontrolled intake of food and is the basis of the pleasure connected with food.

The inhibition of the sense of smell is achieved by various methods and devices.

In particular, the patent application US-A-2005/0037031 describes a method for inhibiting smell using a cream, to be applied inside the olfactory canals, which chemically or physically inhibits olfactory perception by the olfactory epithelium, a thin layer of cells situated in a narrow area of the nasal cavity.

This specific solution, however, has a very short duration in time, since the cream is absorbed by the human body and blown away by the air circulating inside the olfactory channels. This solution is therefore of limited effect.

The patent application US-A-2008/0092896 describes a method of inhibiting smell by a physical obstacle consisting of a stick to be inserted into the nasal cavities.

This device, although much more durable than the use of creams, is very problematic to insert and blocks the sense of smell only very partially.

Similar devices are described in the patent applications A1 US-A2009/250067, US-A-2013/174849 A1 and US-A-2011/100369 A1.

The patent application US-A-2011/0040144 describes a physical mechanical ablation of the olfactory nerve.

This operation is definitive. However, it is also very invasive and is not reversible. Consequently, even after the patient has regained a body mass out of danger, he/she cannot recover the sense of smell.

In this situation the technical purpose of the present invention is to devise a device for at least partially inhibiting the sense of smell and especially the sense of taste resulting from the association of the main taste perceptions operated by the lingual receptors (salty, sweet, bitter, sour and savoury) modulated by the olfactory sensory perception and subsequent hypothalamic and hedonic cortical processing, able to substantially overcome the aforesaid drawbacks.

Within the sphere of said technical purpose, one important aim of the invention is to obtain a device for inhibiting at least partially the sense of smell with a functioning time, which can be set by the patient.

Another important purpose of the invention is to make a device for inhibiting at least partially the sense of smell that is lasting, but not definitive.

Another important purpose of the invention is to make a device for inhibiting at least partially the sense of smell that blocks substantially or totally said sense of smell.

Another important technical purpose of the invention is to make a device for inhibiting at least partially the sense of smell that is not invasive.

A further important technical purpose of the invention is to make a device for inhibiting at least partially the sense of smell that is bio-compatible and antiseptic.

A no less important technical purpose of the invention is to make a device for inhibiting at least partially the sense of smell that is simple and economical to manufacture, use and maintain.

SUMMARY OF THE INVENTION

The technical task and the purposes specified are achieved by a device for inhibiting at least partially the sense of smell comprising a solid body suitable to be placed inside the nostrils, in the vault of the nasal cavity between the upper turbinate and septum so as to superpose the olfactory mucosa causing a temporary anosmia and having a main extension along a main plane in use substantially parallel to the sagittal plane of the human body, the main plane defining a longitudinal direction and a vertical direction lying in the main plane and mutually perpendicular, and a transverse direction perpendicular to the main plane, the solid body has, in the main plane, a main shape comprising: an upper portion extending mainly in the longitudinal direction and comprising a first upper edge substantially flat and aligned with the longitudinal direction, a lower portion protruding at least partially in the vertical direction and downwards, i.e. on the side opposite the first upper edge, a rear portion extending diagonally in relation to the longitudinal and vertical directions and therefore both in the longitudinal direction and rearwards, and in a vertical direction and downwards, the rear portion comprising a second upper edge in direct contact with the first upper edge and extending in a direction inclined at an angle of between 20° and 70° with respect to the longitudinal direction, and wherein the first upper edge extends, in the transverse direction, more than the remaining part of the solid body.

BRIEF DESCRIPTION OF THE DRAWINGS

The characteristics and advantages of the invention are more evident from the following detailed description of preferred embodiments thereof, with reference to the accompanying drawings, in which.

DESCRIPTION OF THE PREFERRED EMBODIMENTS

Figure 1:
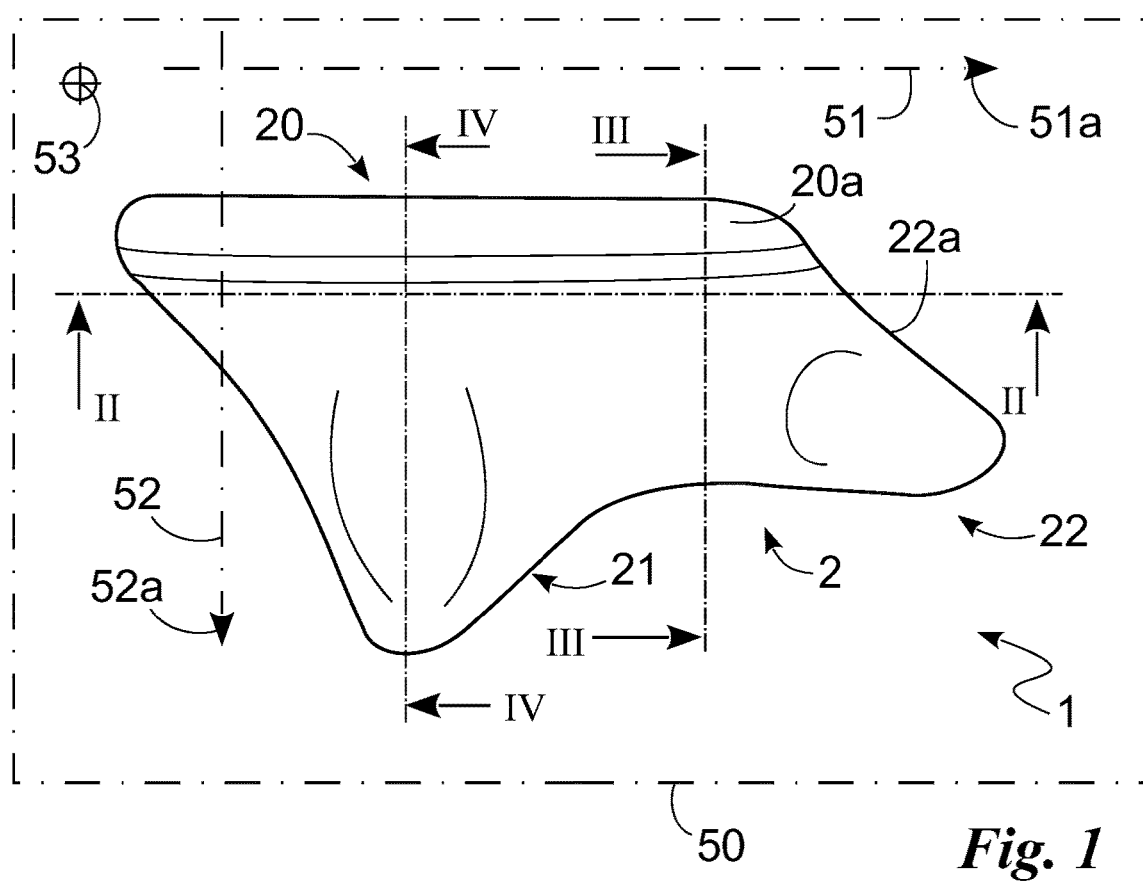
FIG. 1 shows a side view of the device according to the invention.
Figure 2:
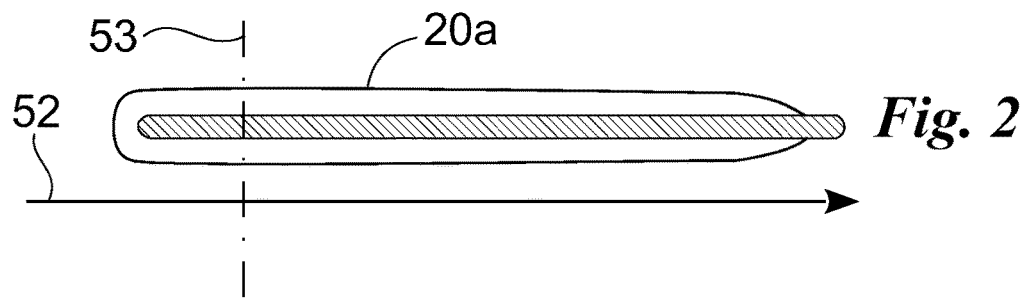
FIG. 2 shows the cross-section II-II indicated in FIG. 1.

Herein, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference which it is associated with. For example, said terms, if associated with a value, preferably indicate a divergence of not more than 10% of said value.

In addition, where used terms such as "first", "second", "upper", "lower", "main" and "secondary" do not necessarily refer to an order, a priority relationship or relative position, but may simply be used to more clearly distinguish different components from each other.

With reference to the Drawings, reference numeral 1 globally denotes the device for inhibiting at least partially the sense of smell according to the invention. It is suitable to be placed inside the nostrils, in the vault of the nasal cavity between the upper turbinate and the septum so as to superpose the olfactory mucosa corresponding to the cribriform plate of the ethmoid, remaining in close contact with the nerve endings causing a temporary anosmia without obstructing the upper nasal cavity.

Preferably, the device 1 comprises two solid bodies 2 described below and illustrated in scale, in a preferred embodiment, in the appended drawings.

The solid body 2 has a main extension along a main plane 50 in use substantially parallel to the sagittal plane of the human body.

The main plane 50 defines a longitudinal direction 51 and a vertical direction 52, lying in the main plane 50 and mutually perpendicular. A transverse direction 53 is also defined perpendicular to the main plane 50, and therefore to the longitudinal 51 and vertical 52 directions.

The vertical direction 52 does not coincide with the gravitational gradient, if not in use and when the patient is upright with his/her head straight. However, the use of the term vertical 52, as also the terms upper and lower, front and back, and horizontal, greatly simplify the reading of this text and have therefore been used herein.

The vectors of the longitudinal 51 and vertical 52 directions are also defined. In particular a downward vector 52a, of the vertical direction 52, and a rear vector 51a of the longitudinal direction 51.

The solid body 2 has a main shape, in the main plane 50 described below. The said main shape is therefore the two-dimensional orthogonal projection on the main plane 50 of the solid body 2 and is illustrated in FIG. 1.

The said main shape mainly comprises an upper portion 20, a lower portion 21 and a rear portion 22.

The upper portion 20, in the main shape, extends mainly in the longitudinal direction 51 and comprises a first upper edge 20a substantially flat and aligned with the longitudinal direction 50.

The lower portion 21, in the main shape, protrudes at least partially, and preferably mainly, in the vertical direction 52 and downwards 52a, indeed the lower portion 21 defines the downward direction 52a, which is on the opposite side to the first upper edge 20a. Again in the main shape the lower portion 21 is preferably tapered downwards, and thus outwards, and approximately in a triangle with bevelled vertex.

The rear portion 22 extends, in the main shape, diagonally relative to the longitudinal 51 and vertical 52 directions and thus extends both in a longitudinal direction 51 and in a vertical direction 52. In particular, in longitudinal directions 51 the rear portion extends in a rear vector 51a, and in longitudinal directions 51, the rear portion extends downward 52a.

Further, the rear portion 22, in the main shape, comprises a second upper edge 22a, in direct contact with said first top edge 20a and preferably connected to the same by a curve. It extends in an inclined direction of an angle between 20° and 70°, more preferably between 30° and 60° and more preferably still between 40° and 50° relative to the longitudinal direction 51. Again, in the main shape the lower portion 21 is preferably tapered outwards, and approximately in a triangle with bevelled vertex.

Also in the front portion, opposite the rear portion and bordering the upper edge 20a and part of the upper portion 20, the body 2 is tapered to a triangle. In the transverse direction 53, the solid body 2, has a smaller extension than in the other directions. In particular, it has a greatly limited average thickness, in the order of 1-3 mm. In contrast, the length in the longitudinal direction 51 is about 25-32 mm, while the height in the vertical direction 52 is about 10-13 mm.

In the transverse direction 53, the first upper edge 20a extends more than the remaining part of the solid body 2, for a thickness preferably comprised between 4 and 6 mm.

The same greater thickness may be extended, in a preferred version, also to the second upper edge 22a.

Figure 3:
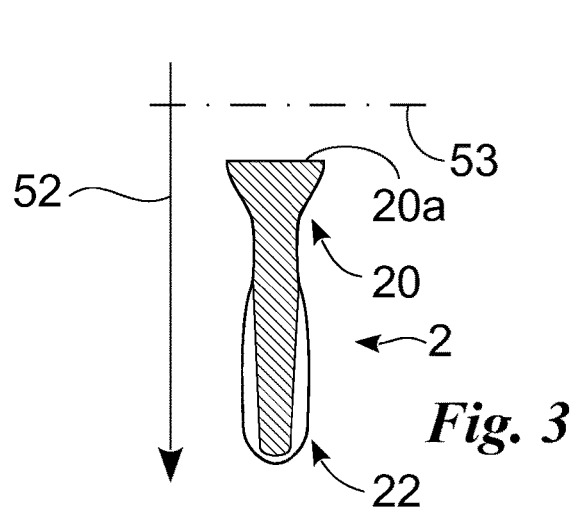
FIG. 3 is the cross-section II-III indicated in FIG. 1.

Furthermore, the rear portion 22 generally has a greater thickness than the average thickness of the solid body, in a transverse direction 53, preferably close to 3-4 mm (FIG. 3).

Figure 4:
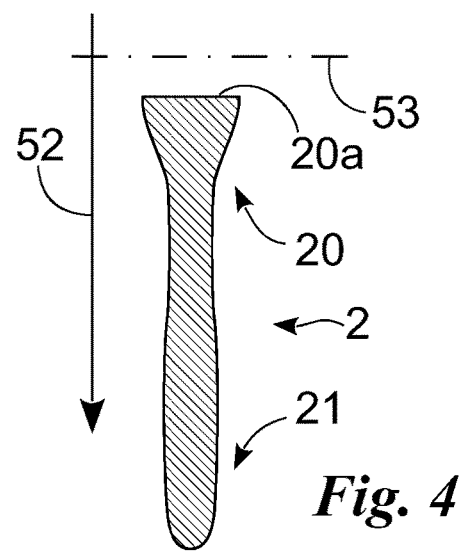
FIG. 4 shows the cross-section IV-IV indicated in FIG. 1.
Figure 5:
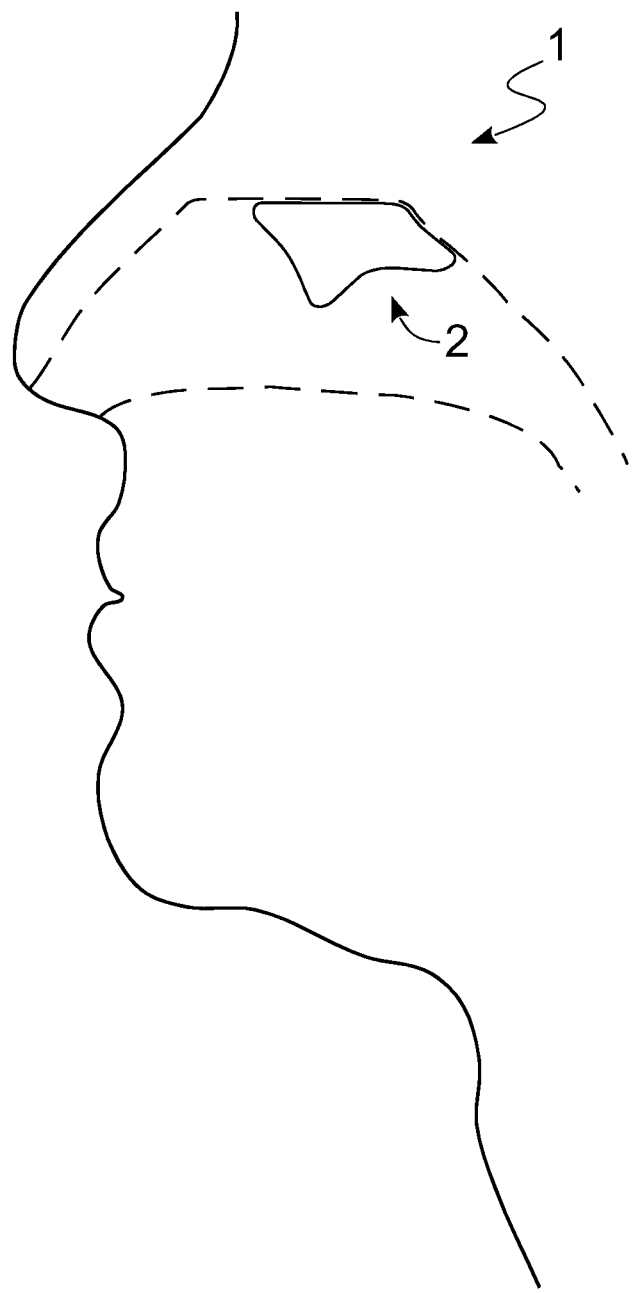
FIG. 5 shows a diagram of how the device according to the invention is used.

In addition, the lower portion 21 generally has a thickness greater than the average thickness of the solid body, in the transverse direction 53, preferably close to 2.5-3.5 mm (FIG. 4).

Finally, the rear portion 22 in the transverse direction 5 has a greater average extension than the average extension in the transverse direction 53 of the lower portion.

The solid body 2 is made predominantly of bio-compatible medical silicone and preferably comprises a surface layer in biopolymer with mucoadhesive and/or preferably antibacterial characteristics. Preferably, the surface layer in antibacterial biopolymer covers at least the first upper edge 20a, which constitutes the outer surface, suitable to meet the olfactory mucosa. Alternatively, the second upper edge 22a or even the entire solid body is also covered with biopolymer with mucoadhesive and/or preferably antibacterial characteristics.

On the first upper edge 20a and/or on the second upper edge 22a drugs may also be placed, absorbable through the nose-brain axis, preferably in turn situated on said antibacterial biopolymer.

The functioning of the device 1 described above in structural terms, is as follows.

Each solid body 2 is inserted into a nasal cavity so that the first upper edge 20a and the second upper edge 22a superpose the olfactory mucosa and prevent the gas particles from reaching the same.

The solid bodies 2 are inserted using tweezers that grip the lower portion 21.

With the insertion of the solid bodies 2 the nostrils are able to absorb the drugs placed on said antibacterial biopolymer and/or of the type described.

The device 1 according to the invention achieves important advantages.

In fact, it inhibits the sense of smell perfectly, thanks to its geometry and materials.

In fact, the olfactory fibres lie in the upper part of the nostril and radiate downwards in a fan shape.

Furthermore, the device 1 can be placed and removed as desired by a doctor using simple tweezers.

It is also comfortable, non-invasive and can also be used to administer drugs.

Variations may be made to the invention described herein without departing from the scope of the inventive concept defined in the claims.

In said sphere all the details may be replaced with equivalent elements and the materials, shapes and dimensions may be as desired.

The invention claimed is:

1. A device for inhibiting at least partially the sense of smell comprising a solid body, configured to be placed inside the nostrils, in the vault of the nasal cavity between the upper turbinate and septum so as to superpose the olfactory mucosa causing a temporary anosmia and having a main extension along a main plane in use substantially parallel to the sagittal plane of the human body, said main plane defining a longitudinal direction and a vertical direction lying in said main plane and mutually perpendicular, and a transverse direction perpendicular to said main plane, said solid body having, in said main plane, a main shape comprising:

an upper portion extending mainly in said longitudinal direction and comprising a first upper edge substantially flat and aligned with said longitudinal direction, a lower portion protruding at least partially in said vertical direction and downwards, i.e. on the side opposite said first upper edge, a rear portion extending diagonally in relation to said longitudinal and vertical directions and therefore both in the longitudinal direction and rearwards and in a vertical direction and downwards, said rear portion comprising a second upper edge in direct contact with said first upper edge and extending in a direction inclined at an angle of between 20° and 70° with respect to said longitudinal direction, and said first upper edge extending, in said transverse direction, more than the remaining part of said solid body.

2. The device according to claim 1, wherein said lower portion in said main plane, is tapered outwards.

3. The device according to claim 1, wherein said rear portion in said main plane is tapered outwards.

4. The device according to claim 1, wherein said rear portion in said transverse direction, has a greater average extension than the average extension in said transverse direction of said lower portion.

5. The device according to claim 1, wherein said first upper edge extends in a direction inclined by an angle comprised between 30° and 60° in relation to said longitudinal directions.

6. The device according to claim 1, wherein said solid body is predominantly made of bio-compatible silicone.

7. The device according to claim 6, wherein at least the first upper edge comprises an outer surface, configured to come into contact with the olfactory mucosa, made of polymer with mucus-adhesive antibacterial characteristics.

8. The device according to claim 1, wherein said solid body comprises a surface layer in polymer with mucus-adhesive, antibacterial characteristics.

9. The device according to claim 8, comprising medicines absorbable through the nose-brain axis and wherein said absorbable medicines are placed on said polymer with mucus-adhesive, antibacterial characteristics.

10. The device according to claim 9, comprising two of said solid bodies, one for each nostril.

* * * * *